United States Patent [19]

Krempl et al.

[11] Patent Number: 4,953,390

[45] Date of Patent: Sep. 4, 1990

[54] METHOD AND A DEVICE FOR MEASURING THE AIR/FUEL RATIO OF AN INTERNAL COMBUSTION ENGINE

[75] Inventors: Peter W. Krempl, Ragnitz; Wolfgang Schindler, Graz; Erich J. Schiefer, Selzthal, all of Austria

[73] Assignee: AVL Gesellschaft für Verbrennungskraftmaschinen und Messtechnik M.B.H. Prof.Dr.Dr.h.c Hans List, Graz, Austria

[21] Appl. No.: 351,215

[22] Filed: May 15, 1989

[30] Foreign Application Priority Data

May 17, 1988 [AT] Austria .................................. 1289/88

[51] Int. Cl.$^5$ .......................................... G01M 15/00
[52] U.S. Cl. ...................................... 73/116; 250/343
[58] Field of Search ............... 73/116, 23; 364/431.05; 250/343

[56] References Cited

U.S. PATENT DOCUMENTS 4,048,479 9/1977 Rivere .............................. 364/431.05
4,733,358 3/1988 Abthoff et al. .................. 364/431.05

Primary Examiner—Jerry W. Myracle
Attorney, Agent, or Firm—Watson, Cole, Grindle & Watson

[57] ABSTRACT

A method and device for delay-free measurement of the air/fuel ratio of combustion systems, especially internal combustion engines, by measuring individual components of the fuel, the ambient air used for fuel combustion, and the exhaust gas, wherein the water vapor concentrations of the exhaust gas and, preferably, the ambient air or the gas supplied for fuel combustion are measured, and wherein the air/fuel ratio are computed by the obtained values and data on fuel composition.

25 Claims, 2 Drawing Sheets

METHOD AND A DEVICE FOR MEASURING THE AIR/FUEL RATIO OF AN INTERNAL COMBUSTION ENGINE

BACKGROUND OF THE INVENTION

The invention relates to a measurement method for lambda and/or the air/fuel ratio of combustion systems, especially internal combustion engines, by measuring and/or analyzing the individual components of the fuel, and the ambient air used for combustion of the fuel, and the exhaust gas, as well as to a device for implementation of such method.

A method of measuring various exhaust gas components, especially CO and HC, is described in Germain laid open No. 25 57 508.

On the basis of such measurements and measurement of the concentration of $CO_2$, lambda and/or the air/fuel ratio may be determined. The disadvantage of this kind of measuring method is, however, that the sensors required are only suited for filtered exhaust gas, which will limit the dynamics of the measuring process, since rapid changes in the measured values cannot be reproduced precisely because of the filter, or, if very small filter units are used, because maintenance or replacement of the filter will be necessary after a very short time.

SUMMARY OF THE INVENTION

It is the object of this invention to avoid the disadvantages of previous methods and to develop a method of the above type in such a way as to permit the required measurements to take place in unfiltered exhaust gases and/or ambient air. Above all, this method should be suitable for measuring lambda in the range of 1 to 10 (20), i.e., for engines preferably operating in the excess air range.

According to the invention this is achieved by measuring the concentration of water vapor in the exhaust gas and, preferably, in the ambient air or the gas supplied for combustion of the fuel, in a conventional manner, for example, by infrared absorption, lambda and/or the air/fuel ratio being computed by means of the values measured and from data on the molecular composition of the fuel obtained by an ultimate chemical analysis of the fuel components.

When hydrocarbon-based fuels are burnt the main combustion products are $CO_2$ and $H_2O$. Assuming complete combustion of the fuel it is essentially possible to compute the excess air upon combustion, i.e., lambda and/or the air/fuel ratio, from the actual $H_2O$ content of the exhaust gas, by comparing the measured value and the theoretical $H_2O$ content of the exhaust gas upon stoichiometric combustion. This method is inaccurate in that the exhaust gas will also contain water vapor resulting from the humidity of the ambient air. Measuring accuracy may be improved by measuring the humidity of the ambient air utilized for combustion, and by entering the value obtained in this way into the computation. In this manner the content of water vapor in the exhaust gas may be corrected by a simple differencing operation.

Lambda is defined as the ratio of the air/fuel ratio actually given in a combustion process to the stoichiometric air/fuel ratio.

$$\lambda = \frac{\text{air mass/fuel mass}_{actual}}{\text{air mass/fuel mass}_{stoichiometric}}. \tag{1a}$$

For computation of lambda and/or the air/fuel ratio the concentration of water vapor in the exhaust gas is computed for a stoichiometric combustion process, i.e., $\lambda = 1$. This computation is based on analysis of the fuel, above all, the C:H:O ratio. If C=1, H will give the relative content of oxygen atoms in mol/mol C in the fuel. For computation of lambda relations are as following:

$$\lambda = \frac{\% H_2O(\lambda = 1)}{\% H_2O(M)} \cdot \frac{Vol(\lambda = 1)}{Vol(m)}, \tag{1b}$$

$$\% H_2O(\lambda = 1) = \frac{100H}{2} / [H/2 + C + (H/4 + C - O/2) \cdot \tag{2}$$

$$\left(4.762 \cdot \left(\frac{100}{100 - LF}\right) - 1\right)] = 100 \frac{H}{2} p_o / \left[\left(\frac{H}{4} + \frac{O}{2}\right)p_o + \frac{H}{4} + C - \frac{O}{2}\right] \text{mit } p_o = 0.21 \cdot \left(\frac{100 - LF}{100}\right),$$

$$Vol(\lambda = 1) = 0.79 + 0.21 \cdot (H/2 + C)/(H/4 + C - O/2), \tag{3}$$

$$Vol(\lambda = M) = (Vol(\lambda = 1) - 1) \cdot \frac{\% H_2O(M)}{\% H_2O(\lambda = 1)} + 1, \tag{4}$$

$$A/F \text{ ratio}(\lambda = 1) = \frac{M_{o2}}{M_K} \left(\frac{H}{4} + C - \frac{O}{2}\right) \cdot \frac{\text{weight(air)}}{\text{weight}(O_2)}, \tag{5}$$

$$A/F \text{ ratio}(M) = A/F \text{ ratio}(\lambda = 1) \cdot \lambda. \tag{6}$$

The second term of the formula (1b) reflects the change in exhaust gas volume produced by the combustion gases. $\% H_2O$ ($\lambda = 1$) signifies the $H_2O$ content for stoichiometric combustion, $\% H_2O(M)$ denotes the content of water vapor in the exhaust gas produced by the combustion of fuel with atmospheric oxygen.

This figure is obtained by correcting the value measured for the total concentration of water vapor in the exhaust gas by the concentration of water vapor in the combustion air. $P_o$ is the content of $O_2$ in percent by volume/100 in the humid ambient air. LF stands for the absolute humidity of the ambient or supplied air in percent by volume $H_2O$. $M_{o2}$ and $M_k$ are the molecular weights of the oxygen molecule $O_2$ and the fuel used. Weight (air) and weight ($O_2$) are the weight of the ambient air or supplied air, and the weight of the corresponding oxygen component per standard volume unit, respectively.

Formulae (1) to (6) apply to fuels with or without an oxygen component. Oxygen is present in fuels based on alcohol, for instance, or in fuels containing alcohol additives. Formulae (3) and (4) give approximations of the exhaust gas volumes for $\lambda = 1$ and $\lambda = M$. From formulae (5) and (6) the air/fuel ratio may be computed.

Preferably, the concentration of water vapor is measured by determining the absorption of electromagnetic radiation in a spectral range of 2.4 to 2.8 μm, or, alternatively, 1.8 to 2 μm, the exhaust gas passing through a measuring cell, and the ambient air or the gas supplied for fuel combustion passing through a reference cell. This kind of procedure will give values which are not only accurate but also most dynamic, since measurement based on the absorption of electromagnetic radiation is precise and dynamic as such, in addition to permitting the measuring process to take place in unfiltered exhaust gas, thus preventing any contamination or delays due to exhaust filters. Besides, a simple differential measurement will help take into account the water content in the ambient air. In the above spectral ranges extinction is mainly due to water vapor, whereas the other combustion gases have hardly any effect. For this reason measurement is not contaminated by other exhaust gas components.

In a preferred variant of the invention the proposal is put forward that the concentration of water vapor be measured with the use of an interference filter in the $H_2O$ band range with a central wavelength of 2.55 to 2.63 $\mu m$ and a half-band width of 2% to 5%, and with a 5% cut-off value at a wavelength of $\leq 2.65$ $\mu m$. Such interference filters have proved particularly well suited for $H_2O$ measurement because of their virtually negligible cross-correlation to $CO_2$, which means that fluctuations in the $CO_2$ content in the exhaust gas will not influence measurement of the water vapor content. Besides, such filters only have small non-linearities in their absorption characteristics, non-linearity in this band range amounting to approximately 10% for $H_2O$ concentrations from 0 to 20 percent by volume in the exhaust gas, there being no influence of temperature on non-linearity.

In a preferred version it is provided that the value measured for the concentration of water vapor in the exhaust gas be corrected by measuring the concentration of carbon particles contained in the sample. Carbon particles in the exhaust gas, such as soot, will cause a certain extinction in the entire infrared range of interest for the measurements, which may produce errors in the measured values based on the absorption of electromagnetic radiation. If the total mass of carbon particles in the sample is known, the individual measurement values may be corrected by means of the carbon absorption coefficient.

For determination of the total mass of carbon particles it will be of advantage to determine the infrared transmission in the spectral range of 3.8 to 4.15 $\mu m$. In this spectral range the other exhaust components generated during combustion have little or no absorption, and the mass of carbon particles may be determined accurately.

It is furthermore of advantage to determine the content of unburnt hydrocarbons in the exhaust gas, and to utilize the obtained value for the computation of lambda and/or the air/fuel ratio. The accuracy of the measured values may be improved by allowing for the content of hydrocarbons in the exhaust gas when lambda and/or the air/fuel ratio are computed.

Preferably, the content of unburnt hydrocarbons is determined by determining the infrared absorption in the exhaust gas, using a spectral range within which the various hydrocarbon components have roughly the same extinction, for instance at 3.465±0.05 $\mu m$, the measured values being corrected by means of the absorption caused by the carbon particles. In the above frequency band the various components of the mixture constituting the unburnt hydrocarbons, are characterized by approximately the same extinction. In this way a measurement value is gained which is largely independent of the composition of the unburnt hydrocarbons. Again, the accuracy of this value may be improved by taking into consideration the absorption caused at this wavelength by the carbon particles in the exhaust gas.

In a preferred version the CO content in the exhaust gas is determined in addition, and is entered into the computation of lambda and/or the air/fuel ratio. If the measuring range is to be extended to include values of lambda $\leq 1$, combustion can no longer be assumed to be complete. Measuring accuracy may be improved, especially in the lesser lambda ranges ($\lambda \leq 1$), by including the CO content in the exhaust gas resulting from incomplete combustion in the computation of lambda and/or the air/fuel ratio, as the measured CO value will correlate with the $H_2$ component of the exhaust gas, at least in a range of $\lambda \leq 1$.

It will be of particular advantage if the CO content in the exhaust gas is determined by measuring the infrared transmission in the spectral range of 4.4 to 4.9 $\mu m$ preferably, and by correcting this value by means of the absorption of carbon particles at this wavelength. In this spectral range the extinction of CO will predominate over the extinction of the other combustion gases. It is again recommended to correct this value by taking into consideration the effect of the carbon particles on extinction.

In a preferred variant of the invention the absolute humidity of the ambient air is measured by an additional humidity sensor, and the value obtained from this measurement is used for correcting the secondary, non-linear changes in the values measured for $H_2O$ concentrations due to the humidity of the ambient air, or rather, the ensuing values obtained for lambda and/or the air/fuel ratio. When the humidity of the ambient air is accounted for by sweeping the reference cell with ambient air used for fuel combustion, it is assumed in first approximation that extinction increases linearly with the concentration of water vapor. As a secondary effect a slight influence on measuring accuracy results from the fact that the calibration curve indicating the dependence of the extinction value on the concentration of water vapor has a non-linearity of approximately 10% in the measuring range. This influence may be compensated by introducing the atmospheric humidity into a correction algorithm. The humidity measurement itself may be performed with the use of a conventional humidity sensor. Correction of the remaining non-linear dependence of the measured extinction value on the $H_2O$ content of the ambient air or the air supplied for fuel combustion may be achieved by a second-degree polynomial.

The invention further relates to a device for implementation of the above method, with a measuring cell traversed by the exhaust gas of the combustion system, a filter and, finally, a detector receiving the radiation of the source being placed in the radiation path of an electromagnetic radiation source one behind the other, the detector being connected with an evaluation unit and a computing unit for computation of lambda and/or the air/fuel ratio. In such a device the central wavelength and half-band width of the filter are tuned to measuring the concentration of water vapor in the exhaust gas, the filter transmitting preferably in the wave range of 2.4 to 2.8 $\mu m$, or, alternatively, in the 1.8 to 2.0 $\mu m$ range. In this wave range radiation absorption is largely effected by the water vapor, and the influence of other components of the exhaust gas is kept at a minimum.

In a preferred version provisions are made for a reference cell swept by the ambient air or the air supplied for combustion, and for a filter disk or a chopper, the measuring cell and the reference cell being placed between the source of electromagnetic radiation and the filter disk or chopper directing the radiation path through the measuring cell and the reference cell alternatingly, the difference between the value measured for the exhaust gas and that for the ambient air being formed in the evaluation unit (6), such that the influence of the humidity of the ambient air on the measured water vapor concentration value or on lambda is compensated automatically. In this variant not more than one radiation source and one detector will be needed. Besides, passing radiation through the measuring cell and the reference cell alternatingly will help avoid measuring errors due to differences in the sensitivities of several detectors.

In a further development of the invention the filter is provided with several filter elements, one of which is tuned to measuring the concentration of water vapor by its particular central wavelength and half-band width, this element transmitting preferably in the wave range of 2.4 to 2.8 $\mu$m, or, as an alternative, in the 1.8 to 2.0 $\mu$m range, and at least one more filter element being tuned to measurement of a further gas component, such as CO, HC or C particles, which additional measurement is used to correct the value measured for the concentration of water vapor and/or the lambda value in a correcting unit located between evaluation unit and computing unit. By including further exhaust gas components measuring accuracy may be improved.

If the filter elements are mounted on a chopper or filter disk, elements designed for measuring various exhaust gas components may be entered into the radiation path one after the other. The filter elements could also be mounted directly on a detector made up of several segments, however, and a chopper could be provided for measurement alternating between measuring cell and reference cell. This would simplify construction of the device and increase its reliability.

A further variant of the invention provides that one filter element be tuned to measurement of the total mass of carbon particles by a suitable central wavelength and half-band width, and that it transmits in a wave range of 3.8 to 4.15 $\mu$m preferably, its central wavelength ranging from 3.9 to 4.1 $\mu$m, and its half-band width being 2 to 5%. The carbon particles contained in the exhaust gas cause a certain extinction in the entire infrared spectrum. Because of this the values measured for the gas components in the exhaust gas may be in error. As there are no marked absorption bands of any other exhaust components in the spectral range around 4 $\mu$m, the infrared absorption in this range is an indicator of the mass of carbon particles. By means of this value the other values, above all that measured for the concentration of water vapor, may be corrected.

It may be furthermore provided that a filter element be tuned to measurement of the content of unburnt hydrocarbons by suitable central wavelength and half-band width, and that it transmits at a wavelength at which the various hydrocarbon components have approximately the same extinction, e.g., at 3.465 $\mu$m, its central wavelength amounting to 3.465$\pm$0.05 $\mu$m and its half-band width to 2 to 5%. In some operational states of combustion systems emission of unburnt hydrocarbon particles may be too high to neglect. In the above frequency band the various components of the mixture making up the unburnt hydrocarbons have roughly the same extinction. In this way a value may be obtained that is largely independent of the composition of the unburnt hydrocarbons. Measuring accuracy may again be improved by taking into account the absorption caused at this wavelength by the carbon particles contained in the exhaust gas.

It will be advantageous if one filter element is tuned to measurement of the CO component by a suitable central wavelength and half-band width such that it transmits in a wave range of 4.4 to 4.9 $\mu$m, its central wavelength being 4.5 to 4.8 $\mu$m and its half-band width 2 to 5%. Especially in the small lambda range ($\lambda \leq 1$) where emission of CO is inevitable, accuracy will improve with the correction of the water vapor concentration values by means of the CO content.

Furthermore, a sensor may be provided, which is connected with the correcting unit and, preferably, with an additional evaluation unit, and which supplies measurement values, for instance, for the pressure and humidity of the ambient air, or the temperature in the measuring cell or reference cell. By measuring further quantities fluctuations in gas density due to temperature or pressure changes may be detected and their influences on the measurement may be taken into account and corrected.

A transmitter delivering constant physical parameters may be provided, which is connected with the correcting unit. This will permit the device to be easily adapted to different operating conditions.

A particular characteristic of the invention provides that the filter or filter element for measurement of the water vapor concentration be designed as an interference filter in the band range of $H_2O$ with a central wavelength of 2.55 to 2.63 $\mu$m and a half-band width of 2 to 5% and a 5% cut-off value at a wavelength of $\leq 2.65$ $\mu$m. Such interference filters have proved particularly suitable for $H_2O$ measurement, as their cross-correlation to $CO_2$ is negligibly small, i.e., fluctuations in the $CO_2$ content of the exhaust gas will not influence measurement of the water vapor content. In addition, such filters have only small non-linearities in absorption, non-linearity in this band range being approximately 10% for $H_2O$ concentrations in the exhaust gas of 0 to 20% by volume.

DESCRIPTION OF THE DRAWINGS

Following is a more detailed description of the invention as illustrated by the attached drawings, in which.

DETAILED DESCRIPTION OF THE PREFERRED EMBODIMENT

Figure 1:
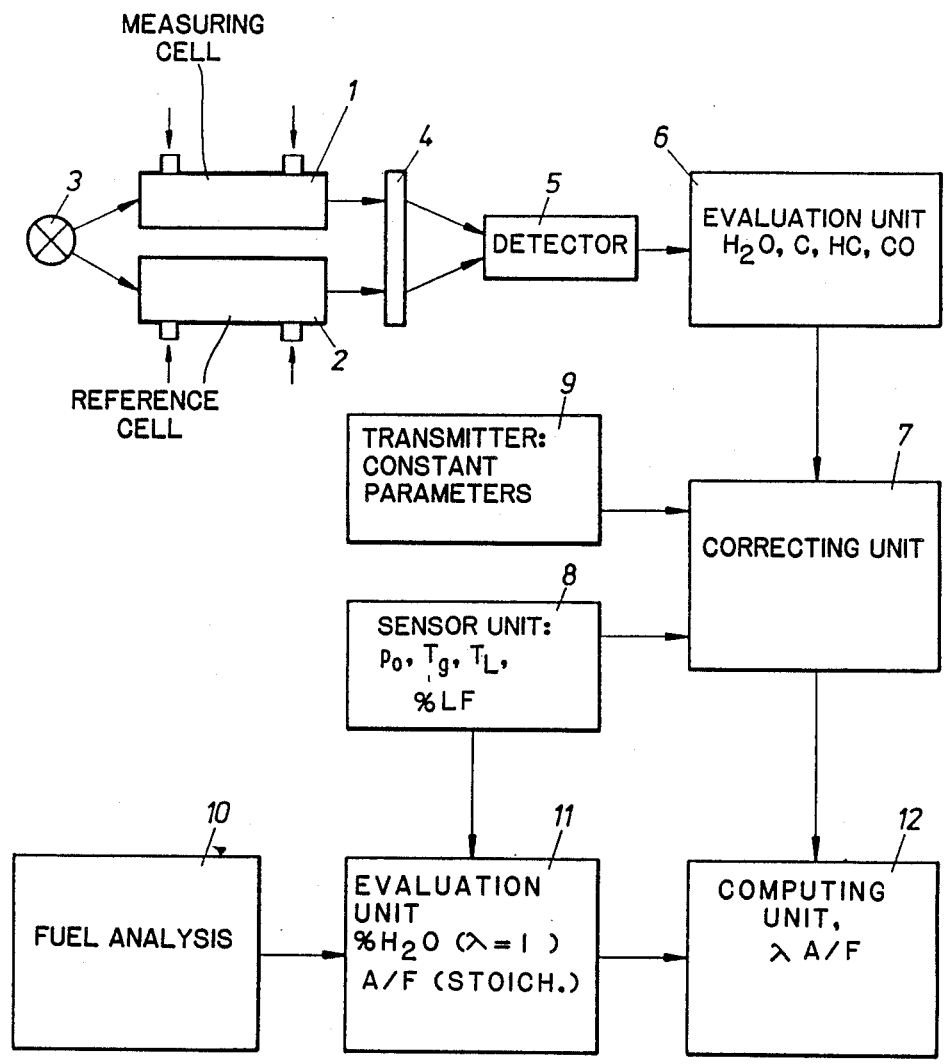
FIG. 1 is a block diagramm of the method and device described by the invention.

The exhaust gas is passed through a measuring cell 1. At the same time ambient air or the air supplied for burning the fuel is passed through the reference cell 2. Electromagnetic radiation, which is generated in an electromagnetic radiation source 3, is first transmitted through cells 1 and 2, and then through a filter transmitting within a narrow spectral range only, which filter is mounted in a filter disk or chopper 4a. If measurements of the mass of carbon particles, HC and/or CO content are to be performed in addition to measuring the concentration of water vapor, provisions are made for a filter disk or a chopper 4a comprising several filter elements 4, each tuned to the particular exhaust component to be analyzed. The intensities of the electromagnetic radiation passing through cells 1 and 2 and the filters are measured one after the other, such that for three interference filters ($H_2O$, C, HC) seven measurement values are obtained; three each for measuring cell 1 and reference cell 2, and one if no radiation is passed through either of the cells. In a detector 5 the intensities of incident radiation are measured. An evaluation unit 6 is employed for determination of the $H_2O$ component in the exhaust gas resulting from the combustion process, i.e., by forming the difference between the intensities in the measuring cell and in the reference cell. In a correcting unit 7 the values measured for the $H_2O$, HC and CO contents in the exhaust gas are corrected by means of carbon particle measurement. Further values entering correction are the temperature $T_k$ of the measuring cell 1, the temperature $T_1$ of the reference cell 2, the ambient air pressure $P_o$, and, if required, the external atmospheric humidity value % LF, which values are provided by a sensor unit 8. In addition, physical constants and parameters are required for correction, which are fed into the correcting unit 7 from a transmitter 9. From analysis of the fuel composition 10 the reference values % $H_2O$ ($\lambda=1$) and the air/fuel ratio (A/F stoich.) in g/g for stoichiometric combustion are computed in an evaluation unit 11.

The computation of reference values also includes the measured values from sensor unit 8. In a computing unit 12 the actual instantaneous lambda and the corresponding air/fuel ratio are determined.

Figure 2:
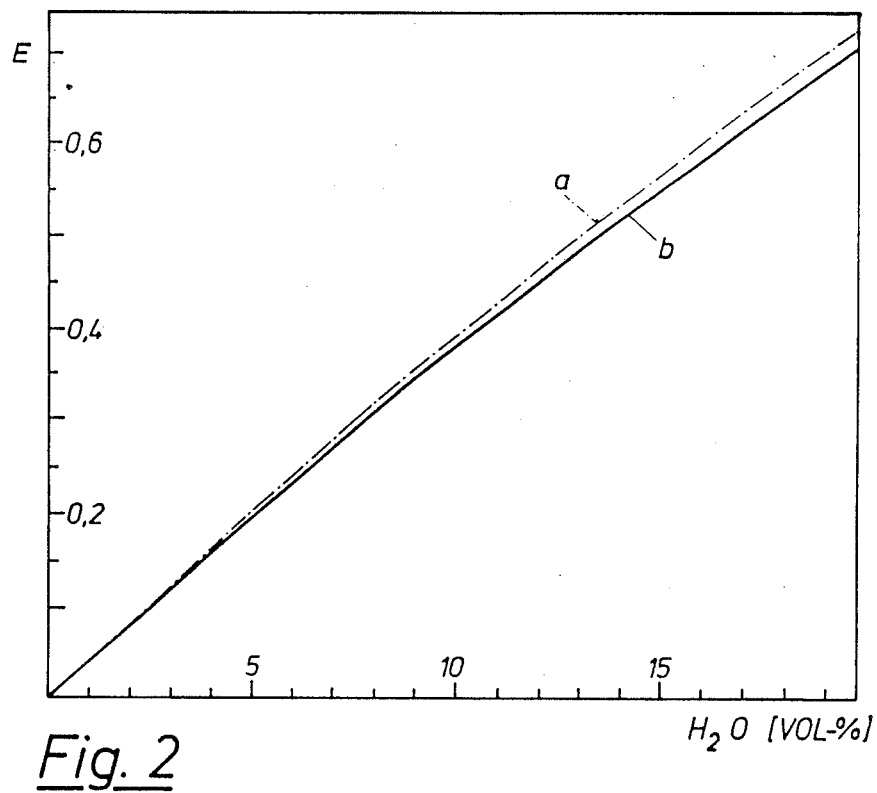
FIG. 2 gives the calibration curve of the interference filter $H_2O$ 001, the dependence of extinction on the $H_2O$ concentration in % by volume.

FIG. 2 gives the dependence of the value obtained for extinction on the $H_2O$ concentration in the exhaust gas for an interference filter with a central wavelength of 2.6 μm and a half-band width of 4% and a 5% cut-off value at a wavelength $\leq 2.65$ μm. The content of water vapor in percent by volume is plotted on the x-axis, extinction as a fractional number is plotted on the y-axis. Curve a was recorded at zero percent humidity, i.e., with dry combustion air, curve b shows the dependence obtained if the ambient air has a content of water vapor of 3% by volume; the extinction value on the ordinate does no longer include the water vapor concentration of the ambient air due to the difference measurement using the reference cell. The percent by volume $H_2O$ of curve b only refers to the exhaust gas components resulting from the combustion of fuel with air.

Figure 3:
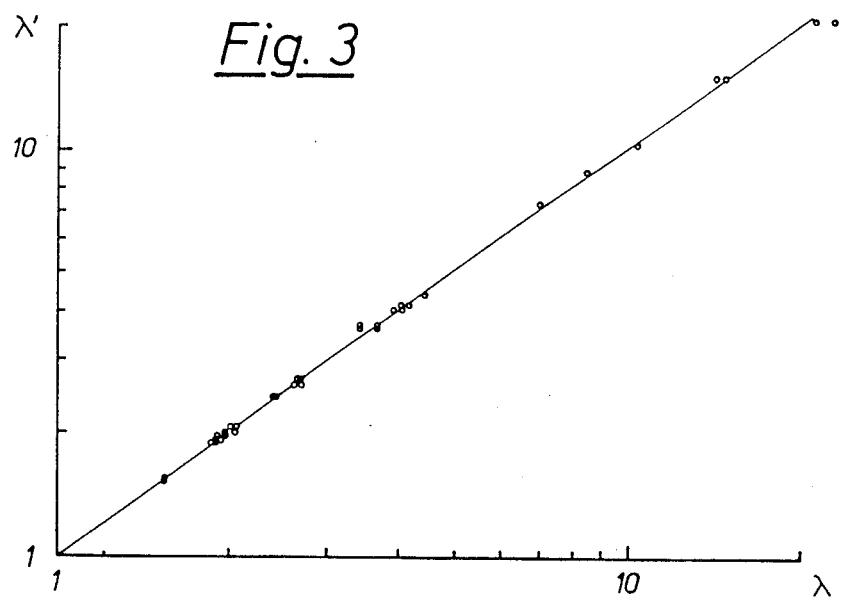
FIG. 3 gives a comparison of lambda values obtained by different measuring methods.

FIG. 3 gives the correlation between the lambda values computed from the measured $H_2O$ concentration values by means of formulae (1) to (4), and lambda values derived from fuel consumption and measurement of the volume of intake air. On the abscissa are plotted the values obtained with the method according to the invention, whereas on the ordinate are plotted the values computed from fuel consumption and measurement of intake air volume. The typical measurement deviation is approximately ±3.5% of the measurement value in the lambda range of 1 to 10.

The method of the invention and the corresponding device have proved to be both simple and robust as well as precise in various test runs, their special advantages being the elimination of exhaust gas filtering and the short response time even for lengthy measurement series.

We claim:

1. A method of measuring the air/fuel ratio (lambda) of an internal combustion engine to which fuel and gas for combustion are supplied and from which an exhaust gas is emitted, comprising the steps of:

(a) analyzing the fuel,
(b) measuring the concentration of water vapor in the exhaust gas,
(c) measuring the concentration of water vapor in the gas supplied for combustion of said fuel, and
(d) computing said air/fuel ratio from said concentration values obtained in steps (b) and (c) and from data on the molecular composition of said fuel obtained by the chemical analysis in step (a).

2. A method according to claim 1, wherein said concentration of water vapor is measured by infrared absorption.

3. A method according to claim 2, wherein said concentration of water vapor is measured by determining the absorption of electromagnetic radiation in one of the spectral ranges of 2.4 μm to 2.8 μm and 1.8 μm to 2 μm, said exhaust gas passing through a measuring cell, and said gas supplied for fuel combustion passing through a reference cell.

4. A method according to claim 3, wherein said concentration of water vapor is measured using an interference filter in the $H_2O$ band range with a central wavelength of 2.55 μms to 2.63 μm and a half-band width of 2% to 5%, wherein said interference filter has a 5% cut-off value at a wavelength of $\leq 2.65$ μm.

5. A method according to claim 1, wherein said value measured for the concentration of water vapor in said exhaust gas is corrected by measuring the concentration of carbon particles contained in said exhaust gas.

6. A method according to claim 5, wherein the total mass of said carbon particles is determined by determining the infrared transmission in the spectral range of 3.8 μm to 4.15 μm.

7. A method according to claim 1, wherein the content of unburnt hydrocarbons in said exhaust gas is additionally determined and the value obtained therefor being entered into the computation of said air/fuel ratio.

8. A method according to claim 7, wherein the content of various unburnt hydrocarbons is determined by determining the infrared absorption in said exhaust gas, using a spectral range within which said various hydrocarbon components have about the same extinction, said values obtained being corrected by means of the absorption caused by carbon particles.

9. A method according to claim 8, wherein the content of unburnt hydrocarbons is determined by determining the infrared absorption at 3.465±0.05 μm.

10. A method according to claim 1, wherein the CO content in said exhaust gas is additionally determined, the value obtained therefor being entered into the computation of said air/fuel ratio.

11. A method according to claim 10, wherein the CO content in said exhaust gas is determined by measuring the infrared transmission in the spectral range of 4.4 to 4.9 μm, and wherein the value obtained is corrected by means of the absorption caused by carbon particles at this wavelength.

12. A method according to claim 1, wherein said gas supplied for combustion is ambient air and wherein the absolute humidity of said ambient air is measured by means of an additional humidity sensor, and the value obtained from this measurement is used for correcting the secondary, non-linear changes in the values measured for said $H_2O$ concentrations that are due to the humidity of said ambient air, or rather, the ensuing values obtained for said air/fuel ratio.

13. A device for measuring the air/fuel ratio (lambda) of an internal combustion engine, comprising:

(a) an electromagnetic radiation source means for emitting a beam of radiation,
(b) a measuring cell traversed by exhaust gas of said combustion engine placed in the beam of radiation,
(c) a filter placed in the beam of radiation having a central wavelength and a half-band width for measuring the concentration of water vapor in said exhaust gas, said filter transmitting in at least one of the wave ranges of 2.4 to 2.8 μm and 1.8 to 2 μm,
(d) a detector, placed in the beam of radiation, and
(e) an evaluation unit and a computing unit for computing said air/fuel ratio, which are connected with said detector.

14. A device according to claim 13, comprising further a reference cell swept by the gas supplied for combustion, and a filter disk, said measuring cell and said reference cell being placed between said source of electromagnetic radiation and said filter disk directing said radiation path through said measuring cell and said reference cell alternatingly, wherein the difference between a value measured for said exhaust gas and a value measured for said gas is formed in said evaluation unit, such that the influence of the humidity of said gas supplied for combustion on the water vapor concentration value is compensated automatically.

15. A device according to claim 14, comprising a reference cell swept by the ambient air.

16. A device according to claim 14, wherein said filter is provided with several filter elements, one of said filter elements is tuned for measuring the concentration of water vapor by its particular central wavelength and half-band width, said filter element transmitting in at least one of the wave ranges of 2.4 μm to 2.8 μm, and 1.8 to 2 μm, at least one of said filter elements is tuned for measuring the further gas components, CO and HC for measuring C particles, all additional measurements are used to correct the value measured for said concentration of water vapor in a correcting unit located between said evaluation unit and said computing unit.

17. A device according to claim 16, wherein one of said filter elements is tuned to measurement of the total mass of carbon particles by a suitable central wavelength and half-band width, transmitting in a wave range of 3.8 μm to 4.15 μm.

18. A device according to claim 17, wherein said filter element tuned to measurement of the total mass of carbon particles has a central wavelength of 3.9 μm to 4.1 μm and a half-band width of 2% to 5%.

19. A device according to claim 16, wherein one of said filter elements is tuned to measurement of the content of various unburnt hydrocarbons by a suitable central wavelength and half-band width, transmitting at 3.465 μm at which said various hydrocarbon components have approximately the same extinction.

20. A device according to claim 19, wherein said filter element tuned to measurement of the content of unburnt hydrocarbons has a central wavelength of 3.465±0.05 μm and a half-band width of 2% to 5%.

21. A device according to claim 16, wherein one of said filter elements is tuned to measurement of the CO component by a suitable central wavelength and half-band width, transmitting in a wave range of 4.4 μm to 4.9 μm.

22. A device according to claim 21, wherein said filter element tuned to measurement of the CO component has a central wavelength of 4.5 μm to 4.8 μm and a half-band width of 2% to 5%.

23. A device according to claim 16, wherein at least one sensor is provided which is connected with said correcting unit and with an additional evaluation unit, said sensor supplies measurement values for at least one parameter of the pressure and humidity of the ambient air, and the temperature in said measuring cell and said reference cell.

24. A device according to claim 16, wherein a transmitter delivering constant physical parameters is provided, which is connected with said correcting unit.

25. A device according to claim 13, wherein said filter or said filter elements for measurement of the water vapor concentration is designed as an interference filter in the H₂O band range with a central wavelength of 2.55 μm to 2.64 μm and a half-band width of 2% to 5% and a 5% cut-off value at a wavelength of ≦2.65 μm.

* * * * *